United States Patent [19]
Evans

[11] Patent Number: 5,662,122
[45] Date of Patent: Sep. 2, 1997

[54] METHOD AND APPARATUS FOR OBJECTIVELY ASSESSING AND CORRECTING THE RELATIVE COMPLIANCE OF VERTEBRAL SEGMENTS

[76] Inventor: Joseph M. Evans, Box 49, R.D. 3, Export, Pa. 15632

[21] Appl. No.: 374,982

[22] Filed: Jan. 19, 1995

[51] Int. Cl.$^6$ .................................................. A61B 3/16
[52] U.S. Cl. .................................... 128/781; 128/652
[58] Field of Search ................................ 128/781, 782, 128/652

[56] References Cited

U.S. PATENT DOCUMENTS

| | | | |
|---|---|---|---|
| 2,532,915 | 12/1950 | Horner | 128/781 |
| 4,479,498 | 10/1984 | Toftness | 128/653 |
| 4,841,955 | 6/1989 | Evans et al. | 127/52 |
| 4,984,127 | 1/1991 | Evans et al. | 361/179 |
| 5,101,835 | 4/1992 | DelRe | 128/781 |

FOREIGN PATENT DOCUMENTS 2168489  4/1988  United Kingdom.

OTHER PUBLICATIONS

Force Recording & Analysis System—Model 01—User's Manual, Sense Technology, Inc., Pittsburgh, Pa., 1993.
Precision Adjustor (Model SHLCP-5-Single Head), User's Manual, Kinetic Technology Inc., Pittsburgh, Pa., 1992.

Primary Examiner—Max Hindenburg
Assistant Examiner—Pamela L. Wingood
Attorney, Agent, or Firm—Jacobson, Price, Holman & Stern, PLLC

[57] ABSTRACT

A method and apparatus allows for simple correction of restricted spinal motion. The clinician applies a uniform low-energy diagnostic impulse to each vertebral segment of interest and the resulting force waveform is recorded. The force waveforms of each diagnostic impulse are compared to determine the relative compliance of each vertebral segment. The clinician then selects the vertebral segment to be adjusted on the basis of identification of fixated or hypomobile segments and high compliance or hyper-mobile segments. Adjusting thrusts are applied in the region of the hypo-mobile segments. The last step may or may not include a comparison of the post-adjustment compliance of the spinal system under analysis with the compliance before adjustments were performed on the spine.

22 Claims, 5 Drawing Sheets

METHOD AND APPARATUS FOR OBJECTIVELY ASSESSING AND CORRECTING THE RELATIVE COMPLIANCE OF VERTEBRAL SEGMENTS

BACKGROUND OF THE INVENTION

1. Field of the Invention

The present invention relates to a chiropractic adjustor. More particularly, the present invention relates to a method and apparatus for assessing and correcting the relative compliance of vertebral segments for use with chiropractic adjustors.

2. Description of the Related Art

Controlled tests of spinal manipulative therapy have not been perceived as satisfying the requirements of investigators. However, spinal manipulative therapy is steadily gaining acceptance as a treatment modality for lower back pain.

Spinal manipulative therapy is any procedure which is used to mobilize, adjust, manipulate, apply traction, massage, stimulate, or otherwise influence the spine and paraspinal tissues with the aim of influencing the patient's health. The major theories on which manipulation is based include the reduction of disc prolapse, the correction of posterior joint dysfunction, the mobilization of fixated or blocked vertebral joints, the reduction of nerve root compression, the normalization of reflex activity, and the relaxation of muscles.

Consideration of the possible effects of manipulation on the structure of the spine has led to the postulation that there exists barriers to motion within the spinal joints which can be influenced by manipulation. A model representing the ranges of motion for each spinal joint is presented in FIGS. 1A to 1D. The "active" range of motion is that motion affected by muscles alone. Here, N designates the neutral position for the spinal joint and MA refers to the limit of muscle activity.

The active range is the range of motion in which normal exercise is performed and which is limited by the leverage capacity of muscles surrounding the joint. Beyond the active range of motion is the "passive" range of motion where external forces are used to effect stretching beyond the "active" range of motion. The limit of the "passive" range of motion, PB, is the so-called "physiologic barrier". Beyond that range is a smaller range of motion through which a joint can be moved without disrupting its ligaments. This range of motion can be entered by a quick thrust in the direction of joint movement. The limit of this range is the "anatomic barrier", AB, beyond which will result in the tearing of ligaments or bony collapse.

Figure 1A:
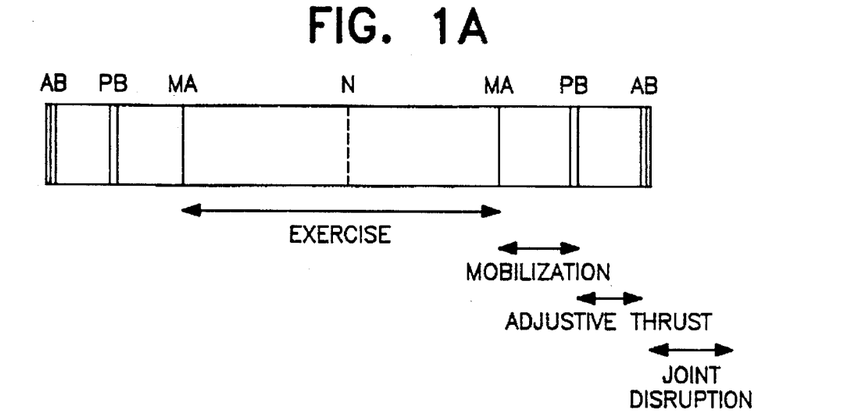
FIGS. 1A–1D show a conceptual model for mobilization and manipulation.
Figure 1B:
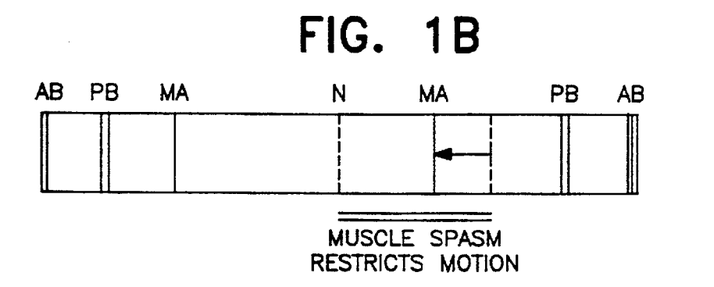
Figure 1C:
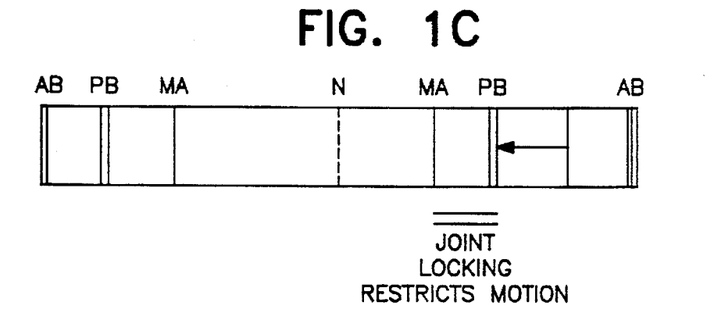
Figure 1D:
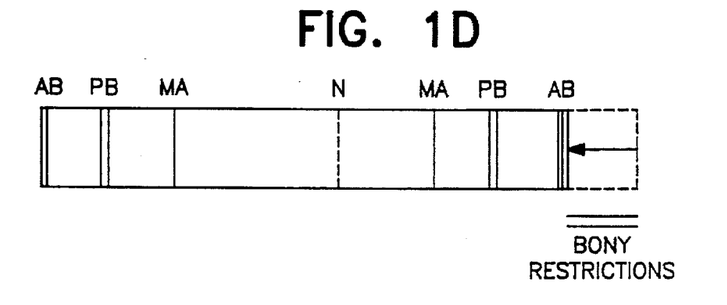

Normal motion, as shown in FIG. 1A, may be restricted in any of three ways which include muscle spasm, joint locking and bony restriction. In FIG. 1B, the muscles surrounding the joint are in spasm and the normal range of motion is restricted. In FIG. 1C, the joint has locked on one side, pulling the physiologic barrier towards the neutral position. Mechanisms for this restriction in motion include articular synovial pinching and disc herniation. In FIG. 1D, the bony structure has blocked movement through spur formation or deformity.

In the first two instances, manipulation may restore motion to the joint through releasing the muscle spasm and/or stretching the shortened muscles. In the instance where the motion is restricted due to joint locking, the motion may be restored by a manipulative thrust into the paraphysiologic space to stretch the ligaments and open facets. Bony obstructions to movement may not be susceptible to manipulation.

Identification of fixated vertebral segments has traditionally been accomplished through manual palpation of the spine and more recently through the observation of spinal motion with X-ray image intensifiers. However, this process requires skill to perform and often is slow and not very accurate.

SUMMARY OF THE INVENTION

Accordingly, it is an object of the present invention to enable an examiner to objectively determine the relative compliance of two or more vertebral segments or to evaluate the mobility of a single spinal segment in any of its degrees of freedom.

Another object of this invention is to objectively evaluate the mobility or compliance of specific vertebrae or spinal segments and to restore fixated segments to normal compliance.

It is a further object of the present invention to provide a device for objectively correcting fixated vertebral segments.

Methodology and apparatus have been developed which enable an examiner to objectively determine and correct the relative compliance of two or more vertebral segments. The invention further enables an examiner to objectively evaluate the mobility of a single spinal segment in any of its degrees of freedom. One embodiment is performed by applying an equal energy impulse to at least two segments of the spine. An energy impulse is received from each segment in response to the equal energy impulse and a force waveform is generated and recorded. A peak force and maximum rate of change of force is extracted with time from each waveform. The force waveform, peak force, and maximum rate of change of force are displayed.

Another method of chiropractic adjusting by objectively assessing the compliance of the spine is achieved by challenging each specific spinal segment with a low and constant energy impulse. The force waveform resulting from that impulse is recorded and the force waveforms generated by the challenging impulses are compared to determine segments of hyper and hypo-mobility. Corrective high energy thrusts are applied to the segments of the spine identified as hypo-mobile.

These and other objects of the invention, as well as many of the intended advantages thereof, will become more readily apparent when reference is made to the following description taken in conjunction with the accompanying drawings.

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

The first step in the present invention is to obtain a measure of the compliance of each vertebra or segment of the spine under evaluation. As will be discussed in more detail below, this measure is obtained by sequentially applying a low-energy impulse to each portion of the spine. Each impulse is composed of equal energy which, in the preferred embodiment, occurs over a one millisecond period.

In response to the applied low-energy impulse, the spinal segment under evaluation will produce an energy response. The energy response is sensed and recorded by the system. Since the low-energy impulse is uniform, variations in the resistance of the spinal structure will define a rate of change of force. Due to differences in the muscular and connective tissues, as well as the size and configuration of the bony structure of individuals, no two persons have the same compliance measurements. These variations in resistance of the spinal segments will result in a corresponding variation in the energy response.

Comparison of the compliance measurements of different segments of the spine will indicate which joints are fixated since the fixated joints will have the lowest compliance. The fixated joints or spinal segments are candidates for spinal manipulative therapy. A rigidly fixed portion or joint of the spine will produce a higher peak force for the same energy impulse than a portion of the spine which is easily moved or compliant. The peak force is defined as the point at which the slope of the rising force impulse is zero. The rate at which force rises from the initial contact to the peak force will vary. The rate of increase will be much steeper with a rigid joint versus a compliant joint. The rate of change, as well as the peak force, is recorded by the system.

The relative compliance of the vertebral segments under examination may be determined by either of two methods. The first method is to extract the maximum force from each force applied versus a time recording made at each vertebral segment. The second method is to take the first derivative of the waveform and select the maximum rate of change of force with time.

Figure 2:
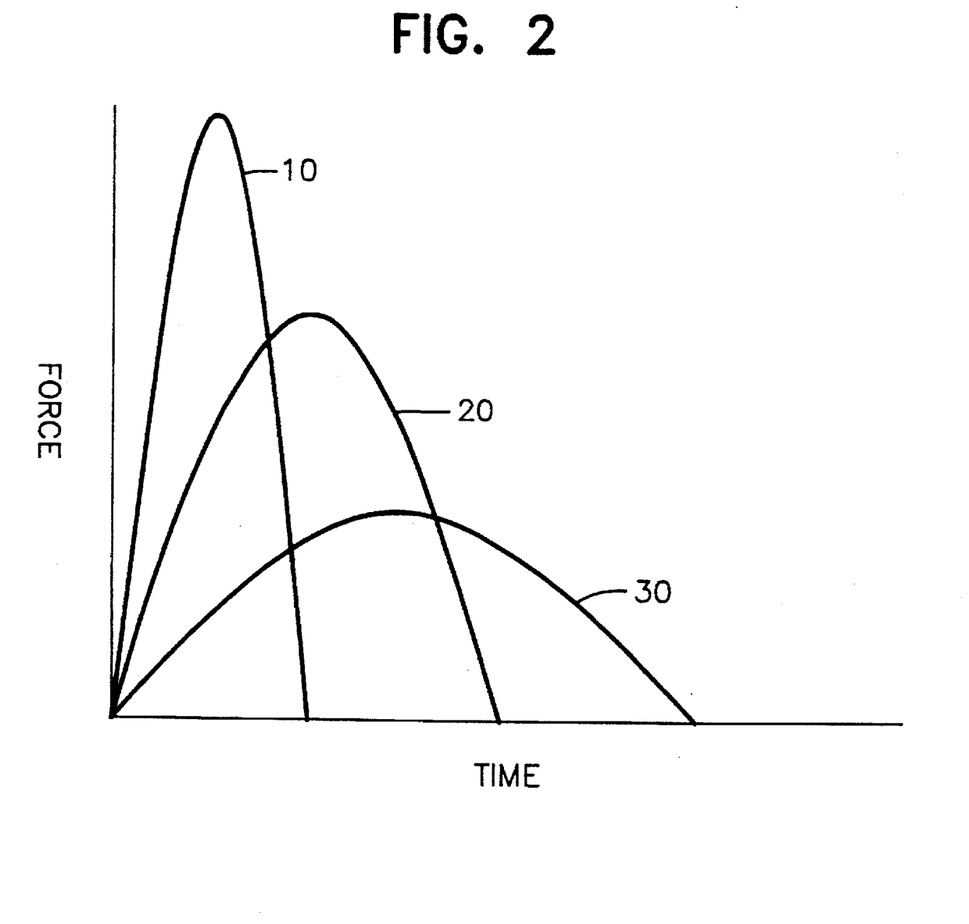
FIG. 2 is a diagram of force versus time response of hard and soft substrate to impulse loads of equal energy imparted on the substrate.

Now referring to FIG. 2, curves 10, 20, 30 show force versus time for response to impulse loads of equal energy on hard, medium, and soft substrates, respectively. The force versus time for curve 10 rises rapidly to a high peak when the impulse energy meets an unyielding or noncompliant object. The rise is slower and has a lower peak when the energy is dissipated into a more compliant or yielding surface, such as shown by curve 30.

The present invention uses the rate of change of force depicted by FIG. 2. After the spinal segments of interest have been challenged with the low-energy impulses and the force versus time waveform have been recorded, the maximum derivative or the maximum peak for each waveform is stored in a buffer. In order to obtain a relative measure of the compliance of the vertebral segments, each maximum is then divided by the maximum slope or peak in the buffer.

This process yields a set of numbers the maximum of which is equal to one. These numbers are then displayed as a graph or as a series of bar graphs identified with the vertebral segment under examination. This display allows the clinician to identify the highest and lowest areas of compliance of the examined spine. This procedure may be repeated for the same segments of spine after adjustment to form an objective record of the effects of the adjustment on the compliance of the spinal segments. The clinician may now objectively determine the relative compliance of selected spinal segments and record and display the results of the analysis.

Therapy is applied with the same instrument by increasing the energy content of the impulse from the low-energy, diagnostic impulse to a therapeutic impulse. The impulse is then applied in the angle and position defined by normal practice for the specific spinal vertebra. The therapeutic impulse may be applied more than once until such time as the appropriate patient response and/or compliance is obtained.

To obtain verification that the joint has been mobilized, the diagnostic impulse procedure is repeated. The energy content of the impulse is returned to diagnostic and the impulse is applied to the same segments of the spine as in the initial diagnostic phase. If the joint has been mobilized, the peak force will have been reduced to a value that is comparable to the other segments of the patient's spine.

Figure 3:
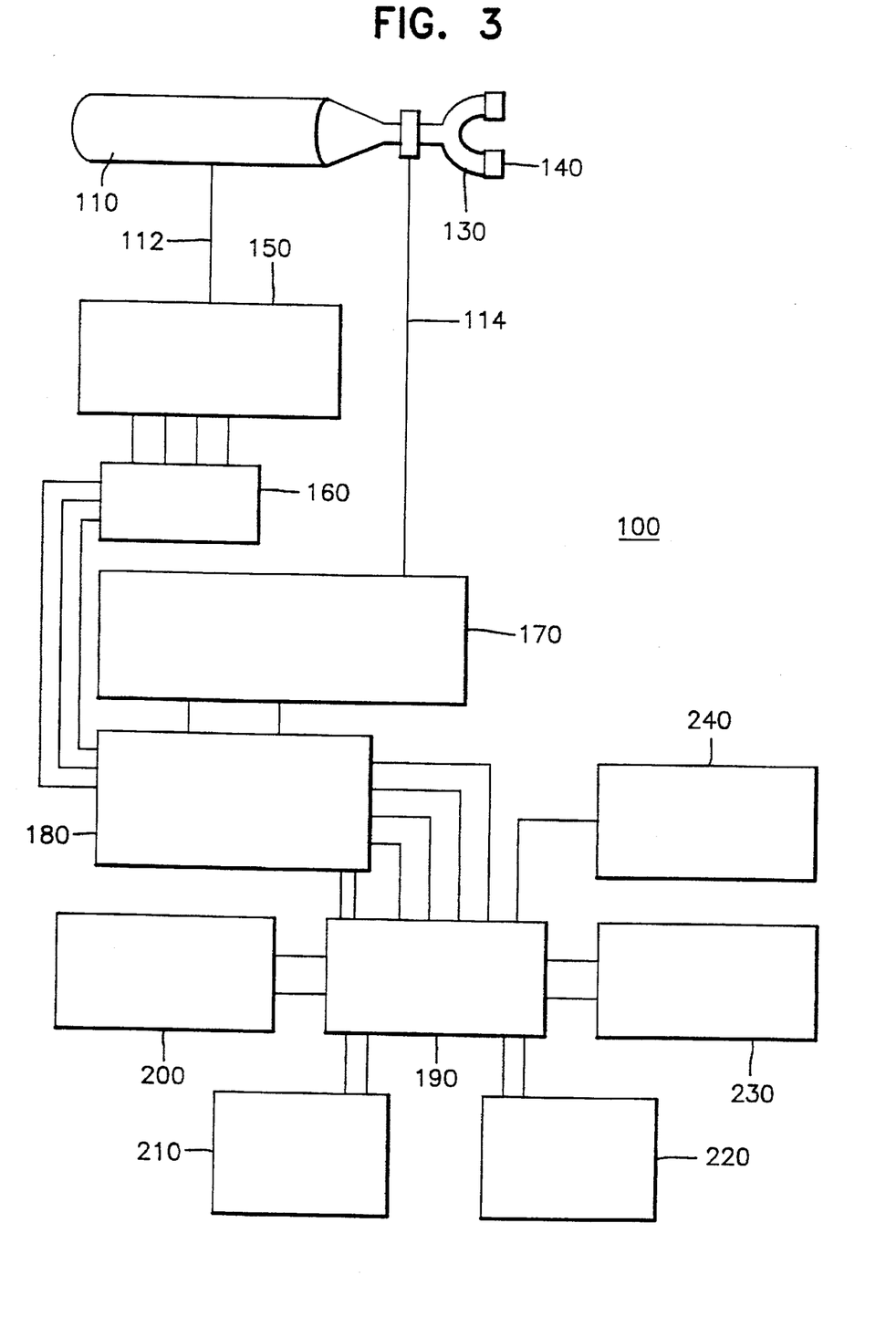
FIG. 3 shows the overall system of the present invention.

Now referring to FIG. 3, the overall system 100 of the present invention is shown. A chiropractor adjustor 110 is used to apply diagnostic impulses, as well as adjustment forces, to the patient. The diagnostic impulses consist of a preselected uniform low-force impulse. In the preferred embodiment, the diagnostic impulse is 15 pounds when the system is calibrated on a standard patient simulator consisting of a #8 rubber stopper produced by Fisher Scientific. The diagnostic impulse is attained by first requiring the examiner to establish a preset pressure against the patient with the instrument. The preset patient pressure (or preload) is used as a set point at which the energy of the impulse is initially transmitted to the patient. Because the energy of the diagnostic impulse is uniform and is delivered at the same preload against the patient's spine, a highly reproducible transfer of energy is achieved.

Adjustor 110 has a force transducer 120 connected between the adjustor 110 and head assembly 130. Force transducer 120 comprises a quartz crystal and is used to measure the spinal response energy. The spinal response refers to the dynamic and short-term static forces imparted by the spinal joint or segment in response to the diagnostic impulse force applied by chiropractic adjustor 110. The force transducer 120 measures the spinal response energy and generates a proportional voltage output on voltage output line 114.

In a preferred embodiment, head assembly 130 comprises a double-pronged tip fork head, which can be used to straddle the spine of a patient. At the end of each prong of head assembly 130 are tips 140 which come in contact with the patient. The center-to-center prong spacings of the fork head are at 20, 30 and 45 mm to accommodate various spinal proportions.

Adjustor 110 may be the adjustor described in U.S. Pat. No. 4,841,955 entitled "Chiropractic Adjustor", which issued on Jun. 27, 1989 to Evans et al. The adjustor illustrated by Evans et al., herein incorporated by reference has a head assembly which comprises a single head and tip. Head assembly 130 having tips 140 is conventional and well known in the art.

Force transducer 120 is connected to a signal conditioning and force transducer excitation element 170 via voltage output line 114. A bi-directional analog-to-digital (A/D) converter board 180 transforms the signals received from element 170 into a digital signal for receipt by Central Processing Unit (CPU) 190. CPU 190 receives the force information and may store it on hard drive 200 or floppy disk 230. The information is further displayed on monitor 210 and may be printed on printer 220. Additionally, a mouse or trackball (not shown) is connected to CPU 190 so that the operator may interact with the display monitor 210. Optionally, monitor 210 may comprise a touch-screen device.

In response to the force information received from transducer 120 on voltage output line 114, CPU 190 sends instructions to the chiropractor adjustor 110. The CPU sends a signal through the bi-directional A/D converter 180 and interface board 160 to the internal electronic board 150. The signal is then sent from the internal electronic board 150 to the adjustor 110 via wire 112. In this manner, CPU 190 controls the force to be sent by the chiropractor adjustor 110 to the patient, as selected by the system operator in the manner detailed below.

The CPU 190 further includes a housing having four LED indicator lights (not shown). The first LED indicates that the power is ON. A second LED indicates that the adjustor is activated. A third LED indicates that the adjustor is ON. The fourth LED signifies that the sensor is OFF, indicating that there is a possible break in lines 112 or 114.

Figure 4:
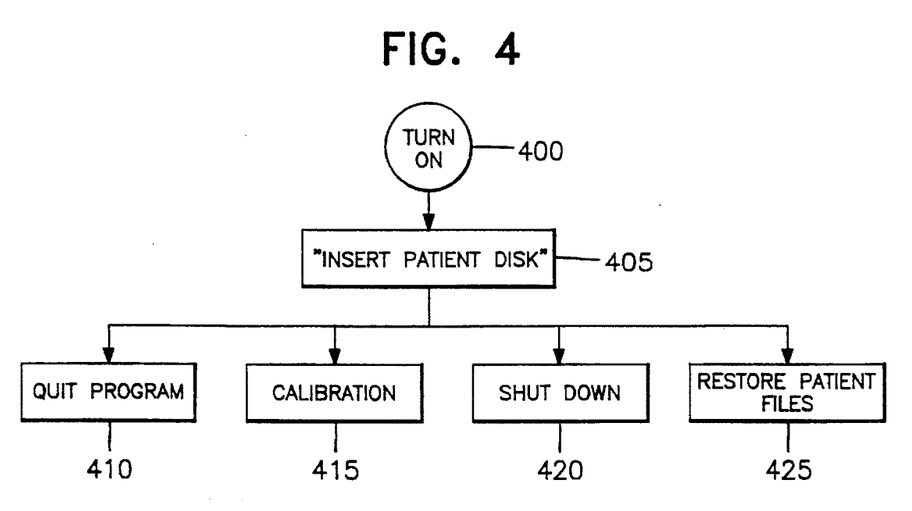
FIG. 4 is a flow diagram of the operation of the invention when the system is first initiated.

The operation of the computer will now be explained with reference to FIG. 4. When the computer is turned on at step 400, a main screen displays the message "INSERT PATIENT DISK" at step 405 on monitor 210. This main screen also displays four additional options: "QUIT PROGRAM" 410, "CALIBRATION" 415, "SHUT DOWN COMPUTER" 420, and "RESTORE PATIENT FILES" 425. The "QUIT PROGRAM" 410 allows the operator to go to the computer operating system. The preferred embodiment uses a Macintosh computer and operating system. In the computer operating system, program updates may be implemented and the interface can be changed.

If the operator selects the "CALIBRATION" mode 415, the operator is able to calibrate the system and chiropractor adjustor 110 before the system is used on the patient. The calibration mode consists of the operator activating the head ten sequential times on a uniform surface. The system takes a mean force of the energy response and checks to see that the forces are within a certain tolerance of each other.

If the operator selects "SHUT DOWN COMPUTER" 420, the files are saved to both the hard drive 200 and floppy disk 230, and the computer prepares itself to be shut off. The hard drive 200 stores the past fifteen visits of that particular patient. If "RESTORE PATIENT FILES" 425 is selected, information from a floppy disk 230 may be downloaded onto the hard drive 200. This would be necessary, for instance, if the hard drive 200 crashes or is otherwise faulty.

Alternatively, the "RESTORE PATIENT FILES" function may be performed by automatically checking the files stored on the patient floppy disk 230 with the corresponding files stored on the hard drive 200. If there are files stored on the floppy disk 230 which are not stored on the hard drive 200, those files will automatically be copied to the hard drive. This process obviates the need to restore patient files which have been inadvertently removed from the hard drive and makes it possible to use the patient disk on any computer in the office or at any other office.

Figure 5:
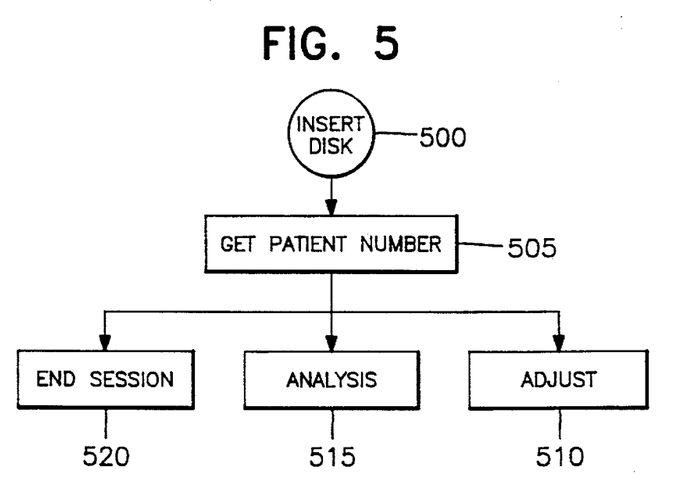
FIG. 5 is a flow diagram of the main options available to the operator of the system of the present invention.

Now referring to FIG. 5, once a floppy disk 230 is inserted, step 500, three results are possible. If the disk has not been formatted, a message will appear saying that the disk is unreadable. The computer will then ask the operator whether the disk 230 is to be formatted.

If the disk 230 is properly formatted but no patient number has been entered, a new patient entry panel having a numeric keypad is displayed. The operator may then enter a new patient number and the program will check to see that the entered number has not been previously assigned to another patient. If it has been assigned to another patient, the program will ask the operator whether or not to format a second disk for the same patient.

If the inserted disk 230 is properly formatted and a valid patient number has been obtained at 505, the program continues to the main analysis panel 600, which corresponds to the main portion of the program of the present invention. At main analysis panel 600, the operator may begin the collection of patient data. In the main analysis panel 600, the operator has the option of adjusting the patient at step 510, performing an analysis at step 515, or ending the session at step 520. These operations are described in relation to FIG. 6 immediately below.

Figure 6:
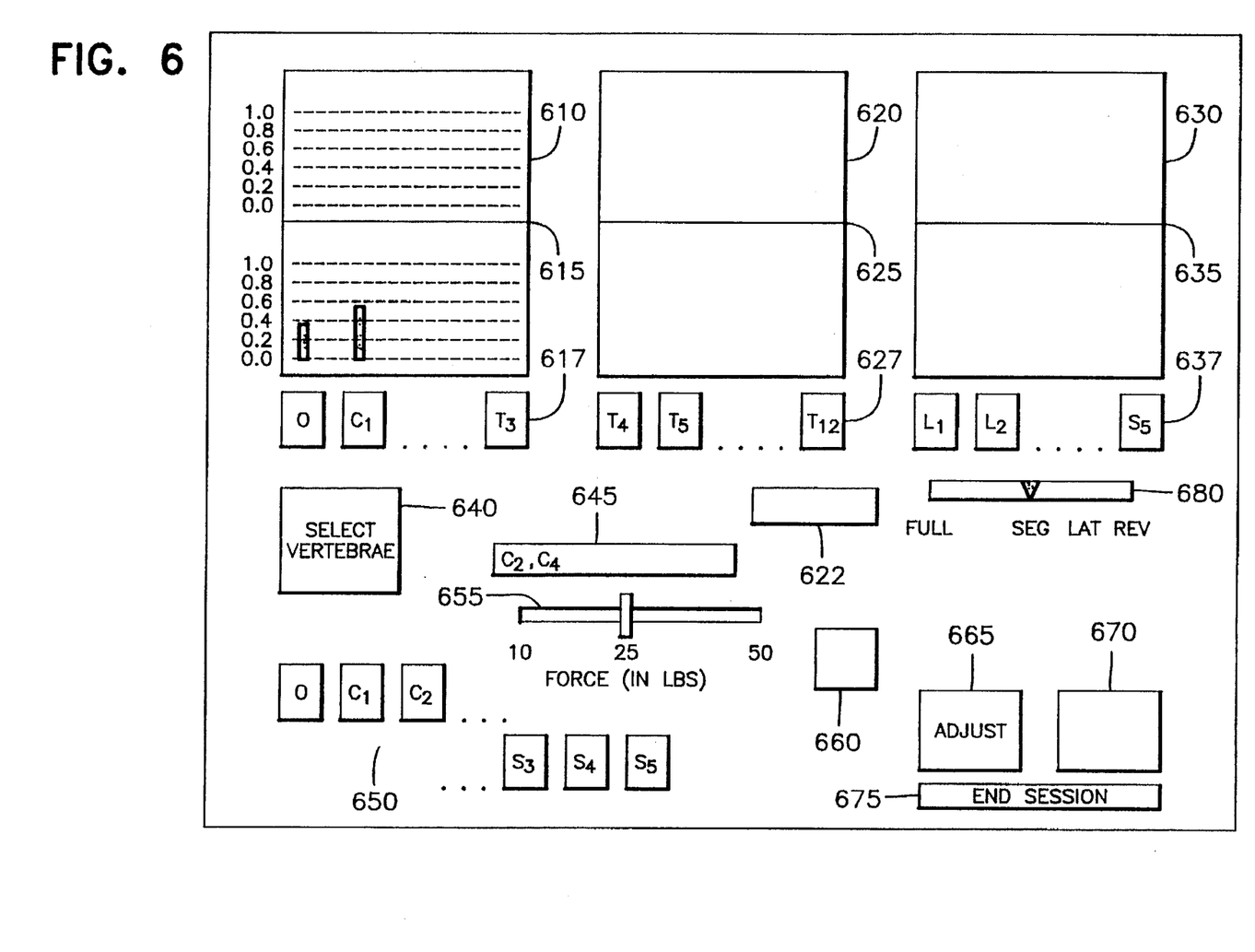
FIG. 6 shows the main analysis panel through which the operator interacts with the overall system.

Now referring to FIG. 6, the main analysis panel 600 is shown having three display areas 610, 620, 630 corresponding to the cervical, thoracic or lumbar regions, respectively. Each display area 610, 620, 630 has an upper and lower display portion separated by display bar 615, 625 and 635, respectively. Directly below each of the display areas 610, 620 and 630 are located groups of spinal indicators 617, 627 and 637, respectively. Spinal indicators 617 correspond to the cervical spinal portions occiput, C1 and C2 through to T3. Likewise, spinal indicators 627 correspond to thoracic spinal portions T4 through T12 and spinal indicators 637 corresponds to lumbar spinal portions L1 to S5.

To begin patient analysis 515, the operator selects any of the display areas 610, 620, or 630 by clicking on the desired display area. In the present example, the operator clicks on display area 610. The display area 610 is now the active display area as will be indicated by a change in color of display bar 615 from yellow to blue. Likewise, the first of the spinal indicators 617, here the indicator corresponding to the occiput, turns from yellow to blue and the system emits an audible beep. If the operator decides not to run a patient analysis, he just clicks on the indicators 617. The indicators 617 will clear through so that no reading will be taken and the system is ready for further functions.

In the present example, the occiput spinal indicator 617 turns blue, indicating that the system is ready to begin an analysis. The clinician first palpates the patient's spine to locate the proper position for analysis. The operator then proceeds to place adjustor 110 onto the desired position of the patient's spine. Upon pressing the adjustor 110 against the patient, the adjustor 110 is automatically activated to apply a single low force diagnostic impulse to the patient. In response to the diagnostic impulse, the transducer 120 receives a response from the occiput of the patient's spine.

The system records the response from the occiput, and the next spinal indicator 617 (C1 in the present example) turns from yellow to blue. Likewise, the occiput indicator 617 turns from blue back to yellow. Thus, the system indicates that it is ready to impart the next diagnostic impulse to C1 of the patient's spine. In this manner, the operator proceeds to apply sequential forces to the remainder of the cervical spinal portion, corresponding to display area 610. As each force is applied, the system records the response signal from transducer 120 and spinal indicator lights 617 scroll until the last spinal portion is applied and recorded. Additionally, the system emits an audible beep after each reading is made, indicating that the system has stored the information and is ready for application of the next diagnostic impulse.

After all of the inputs have been received for the given display area 610, CPU 190 will normalize all of the readings to the highest reading of that section, as described above. The results of this normalization will be displayed on the lower portion of display area 610. For instance, if the response received from vertebrae C2 has the highest energy, it will be indicated as a normalization of one. Accordingly, each of the remaining vertebrae will indicate a relative responsive energy in relation to C2.

By displaying this information, the operator may check for variations in response to the uniform diagnostic energy impulse applied to each of the vertebrae. High responses indicate that the structure does not move as fast as the others and may be fixated. A low response may indicate that a particular vertebrae is compensating for a nearby fixation.

Based on the energy responses, patient history, patient complaints, palpitations to patient, abnormalities between joints, still X-rays and motion X-rays, the doctor may select a vertebrae which is to be adjusted, step 510. The clinician then selects the "SELECT VERTEBRAE" 640 followed by the selection of the vertebral segments from select indicators 650 that are to be adjusted. The clinician is to select the vertebrae based on the order in which he wishes to adjust each vertebrae. As each of the desired indicators 650 are selected, the order and vertebrae to be adjusted is displayed in queue display 645. Alternatively, the "SELECT VERTEBRAE" 640 button may be eliminated so that the operator may begin the selection process simply by selecting the specific vertebrae.

In addition, three buttons, MANUAL, LEFT, and RIGHT (not shown) may be provided in order to more precisely indicate the particular vertebral selection. For instance, pressing the LEFT button and then selecting segment C1 will select the left side of C1. This is particularly applicable where a single prong tip 140 is used with head assembly 130.

After the selection is made, the clinician activates the "ADJUST" button 665. A beep indicates that the program is ready to proceed. In addition, display area 660 indicates the current vertebrae from queue display 645 which is currently being adjusted.

The clinician selects the proper force to be applied by sliding the bar of force selector 655. The clinician then chooses the proper line of drive and point on the spine to be adjusted and applies the adjusting instrument 110. The adjusting instrument 110 is to be smoothly pressed against the patient's spine. The instrument will activate when the preset contact pressure is obtained and will provide multiple rapid adjustments. The clinician may stop the adjusting procedure at any time or may wait until the spinal segment stabilizes, at which time the system will automatically cease.

This invention provides the clinician with a termination procedure which operates in addition to the exercise of clinical judgment. This termination procedure is built upon the concept that the adjustment is effectively complete when a condition of joint stability is obtained. Each adjustment impulse produces a energy response force waveform on the output line 114 of the force transducer 120. As stated above, this force waveform is recorded with the use of the bi-directional A/D converter 180 and a digital computer CPU 190. The maximum or peak value of the force waveform is extracted and compared to previous force waveforms in the current adjustment sequence.

Various methods can be defined to make this comparison. One example is to compare the current peak force for the last adjustment impulse to the average of the previous five waveforms. If the difference is within acceptable limits, the condition of stability is felt to be achieved and the adjustment is stopped. A second and more reliable method is to compare the average of the last three adjustments with the average of all preceding adjustments. This method of comparison would lessen the likelihood that random variations in the current adjusting sequence would fall within a predetermined tolerance level.

The tolerance level is determined by holding the adjustor in an activated position for one hundred repetitions, ten separate times. The maximum value of each repetition is recorded and a three point and five point running average is calculated. The maximum value of the difference between the averages is used as the tolerance level. The difference ranges from 0.001 pound force to 0.008 pound force over the force range of ten to thirty-five pounds.

This methodology provides the clinician with an objective termination procedure for a multiple impulse adjustment. The procedure relies on the measurement of the peak force during each adjustment impulse. The criteria for termination is based upon the concept of joint stability. Stability is obtained at the point in which the underlying structure no longer moves under impulse. Stability is reached when a minimal change in peak force between adjusting impulses is such that the adjuster impulse is essentially constant in energy response output. When the spinal segment being adjusted has stabilized, the adjustment is terminated. After the selected vertebrae has been adjusted, the vertebrae and the number of force applications required for correction will be indicated in display area 662.

If the clinician wishes to stop the adjustment procedure, he does so by removing the adjusting instrument from the patient's spine. The vertebrae and the number of force applications performed will be indicated in display area 662. In this case, the clinician may then proceed to the next spinal segment by selecting the "CLEAR ADJUST" button 670. This will cancel the adjust program and either go to the next vertebral segment to be adjusted or the program will end if no more segments are in queue display 645.

An exception to this is when the patient disk with the number "0000" (ie, four zeros) is used. In this case, a "NEW PATIENT" button (not shown) is added to the display. This allows the clinician to perform an analysis and adjustments on several patients without having to switch floppy disks. Rather, the clinician merely selects the "NEW PATIENT" button after each patient is evaluated. This will clear the screen and save the information for the first patient, and allow the clinician to proceed to the next patient evaluation. In this mode, selecting "ADJUST" without selecting any vertebra will enable the clinician to adjust ten vertebrae in any order without recording the results. Selecting the "CLEAR ADJUST" button 670 will cancel all of the adjustments that have not been completed. In an alternative embodiment, the operator is not limited to ten adjustments. Rather, the operator may continue to adjust any number of times until the "CLEAR ADJUST" button 670.

After all of the vertebrae in the queue have been adjusted, the clinician may now go to another segment of the spine for analysis and adjustment by clicking in either the thoracic or lumbar display areas 620, 630. Or, the clinician may recheck the cervical area by clicking on cervical display area 610. In general, it is beneficial to allow the spine to rest by going to other areas before performing a post-adjustment analysis.

The clinician may retest each of the vertebrae in the section for normalization by performing a post-adjustment analysis. This is done by clicking on the lower portion of display area 610. This moves the results from the pre-adjustment analysis to the upper portion of display area 610. The clinician may then proceed to re-perform the tests in the same manner as initially performed, where the same diagnostic impulse will be used.

The results of the post-adjustment analysis will be displayed on the lower portion of display area 610. Thus, the post-adjustment compliance may be easily compared with the pre-adjustment compliance measurements. The post-adjustment results should be a relatively straight line since any problem vertebrae should have been corrected by the multiple adjustment energy forces.

From main analysis panel 600, the clinician may optionally select to go to a full view, a lateral view, or to review patient files. This is performed by selecting the desired mode from mode selector 680. FIG. 6 shows the selected mode to be the "SEG" or segmented view. Suppose, however, the clinician wishes to evaluate the lateral response of a particular vertebral segment. This may be done by clicking the cursor over the "LAT" position of mode selector 680. When activated, the lateral analysis panel is displayed (not shown). The lateral response panel is similar to main display panel 600. However, the lateral response panel only has a single display area as opposed to the display areas 610, 620, 630 as shown in FIG. 6. The single display area has an upper and lower portion. However, the single display area only has a left and right indicator, instead of the multiple indicators of groups 617, 627 and 637 shown in FIG. 6.

The procedure followed for the lateral analysis panel is similar to that performed with the main analysis panel 600. The spine is palpated to locate the spinal segment of interest. For the lateral analysis panel, a single tip adjustment head (not shown) is used with adjustor 110. The tip is placed on the left side of the patient's spine and pressed smoothly until the instrument activates. The instrument is then positioned on the right side of the same spinal segment and the instrument 110 is again activated.

The lateral response display displays the relative lateral compliance of the vertebral segment on the left as compared to that on the right. If an adjustment is to be made, the clinician may do so without leaving the lateral response panel. Post-adjustment lateral responses may be observed by repeating the above steps.

Another display mode that may be selected by mode selector 680 is a cervical view (not shown). In this view, three cervical display panels are labelled neutral, left and right, respectively. The neutral display panel is used to check the compliance when the neck is in flexion (bent forward) to the maximum range of passive motion. The right display panel checks compliance when the neck is in flexion and twisted to the right. And, the left display panel checks compliance when the neck is in flexion and twisted to the left.

Alternatively, the clinician may review the patient file by selecting "REV" from mode selector 680. The "REV" option will only appear at mode selector 680 when there is a valid patient number. One of skill in the art will recognize that the "REV" option may be provided as a separate button. In this mode, the clinician can review and print out a displayed summary of the patient data recorded during prior clinical sessions. The computer extracts and displays the date of visit, number of adjustments given to each vertebrae and the force level used for that adjustment. The data is displayed in a chart at the bottom of the display. A similar chart containing information for the visits will be printed by activating a print button. The clinician may scroll through the particular information of each visit by selecting a "LAST VISIT" button (not shown). This will display the adjustments made in display areas 610, 620 and 630.

The clinician may optionally select a full view by positioning the cursor above the "FULL" of the slide controller of mode selector 680. In full panel display, the entire length of spinal vertebrae are displayed in one large display area. Essentially, the full panel display combines each of display areas 610, 620 and 630 to provide a single long display.

After treatment is complete, the clinician may select "END SESSION" 675, step 520, to terminate the patient's session. The system will store the patient information from the hard drive 200 to the floppy disk 230. The hard drive 200 stores the past fifteen visits of that particular patient. The program will then return to the "INSERT PATIENT DISK" panel, corresponding to step 405 of FIG. 4 and the floppy disk will be ejected from the floppy drive.

Having described the invention, many modifications thereto will become apparent to those skilled in the art to which it pertains without deviation from the spirit of the invention as defined by the scope of the appended claims.

I claim:

1. A method of determining the relative compliance of spinal segments by:

(a) applying an equal energy impulse to at least two spinal segments, (b) receiving an energy impulse response from each spinal segment, (c) generating a force waveform in response to the energy impulse response received from each spinal segment, and (d) determining the peak force and the maximum rate of change of force with time from each force waveform.

2. The method of claim 1, further comprising the step of:

(e) determining a normalized magnitude.

3. The method of claim 1, further comprising the step of:

(e) correcting the compliance of a spinal segment by applying an adjustment force based upon the force waveform, peak force, and maximum rate of change of force.

4. The method of claim 3, further comprising the step of:

(f) repeating steps (a) to (d) to obtain a post-adjustment analysis.

5. A method of determining the compliance of a spinal segment by:

(a) applying a diagnostic energy impulse to at least one spinal segment, (b) receiving an energy impulse response in response to the diagnostic energy impulse, and (c) determining the peak force and the maximum rate of change of force with time for the energy impulse response.

6. A method of correcting the compliance of a spinal segment by:

(a) applying a diagnostic mechanical energy impulse having a known energy preload to at least one spinal segment, (b) receiving a response from the at least one spinal segment responsive to the diagnostic mechanical energy impulse, (c) determining the compliance of the at least one spinal segment based upon the received response, and (d) applying an adjustment force to the spinal segment based upon said determination.

7. The method of claim 6, wherein the step of applying an adjustment force comprises the step of applying multiple adjustment forces.

8. The method of claim 7, further comprising the steps of:

(e) determining the peak force for each adjustment force, (f) comparing the peak force with the peak force for previous adjustment forces, and (g) terminating the step of applying multiple adjustment forces based upon said comparison.

9. A method for determining the compliance of a spine by:

(a) performing a pre-adjustment analysis, wherein the pre-adjustment analysis comprises the steps of applying a mechanical energy impulse having a known preload to at least one spinal segment and determining the compliance of the at least one spinal segment based upon a received response, wherein the preload preload is such that the impulse imparts a preset energy to the spinal segment, (b) correcting any deviation in compliance by applying an adjustment force based upon the pre-adjustment analysis, (c) performing a post-adjustment analysis, wherein the post-adjustment analysis comprises the steps of applying a mechanical energy impulse having a known preload to the at least one spinal segment and determining the compliance of the at least one spinal segment based upon a received response, wherein the known preload is such that the impulse imparts a preset energy to the spinal segment, and comparing the pre-adjustment analysis with the post-adjustment analysis.

10. The method of claim 9 wherein the pre-adjustment and post-adjustment analysis each comprise the steps of:

(e) applying an equal energy impulse to at least two spinal segments, (f) receiving an energy impulse response from each spinal segment, (g) generating a force waveform in response to the energy impulse response received from each spinal segment, and (h) determining the peak force and the maximum rate of change of force with time from each force waveform.

11. The method of claim 5, further comprising the step of:

(d) correcting the compliance of a spinal segment by applying an adjustment force based upon the peak force and maximum rate of change of force.

12. The method of claim 5, wherein the diagnostic energy impulse is a low-energy mechanical force that physically challenges the at least one spinal segment.

13. The method of claim 6, wherein the diagnostic energy impulse is a low-energy mechanical force.

14. The method of claim 6, wherein the adjustment force is stronger than the diagnostic mechanical energy impulse.

15. An apparatus for correcting the condition of a joint comprising:

means for imparting at least one diagnostic mechanical impulse having a known preload to the joint, wherein the known preload is such that the impulse imparts a preset energy to the joint;

means for receiving a response from the joint responsive to the at least one diagnostic mechanical impulse;

means for determining the condition of the joint based upon the received response; and, means for imparting at least one adjustment force to the joint based upon said determination.

16. The apparatus of claim 15, wherein the diagnostic impulse is a low-energy mechanical force.

17. The apparatus of claim 15, wherein said means for receiving comprises a force transducer.

18. The apparatus of claim 15, wherein said means for imparting a diagnostic mechanical impulse and said means for imparting an adjustment force comprise a single adjustor.

19. The apparatus of claim 15, wherein the adjustment force is a greater force than the diagnostic mechanical impulse.

20. The method of claim 6, wherein the known preload is established by imparting the impulse upon recognition of a predetermined pressure to the spinal segment.

21. The method of claim 9, wherein the known preload is established by imparting the impulse upon recognition of a predetermined pressure to the spinal segment.

22. The apparatus of claim 15, wherein the known preload is established by imparting the impulse upon the application of a predetermined pressure to the spinal segment by said means for imparting at least one diagnostic mechanical impulse.

* * * * *